US005437982A

United States Patent [19]

Catterall et al.

[11] Patent Number: 5,437,982

[45] Date of Patent: Aug. 1, 1995

[54] METHODS OF IDENTIFYING SPECIFIC INACTIVATION GATE INHIBITORS OF THE SODIUM CHANNEL

[75] Inventors: William A. Catterall; Galen Eaholtz, both of Seattle, Wash.

[73] Assignee: University of Washington, Seattle, Wash.

[21] Appl. No.: 118,135

[22] Filed: Sep. 8, 1993

[51] Int. Cl.[6] .......................................... G01N 33/53

[52] U.S. Cl. .......................................... 435/7.2; 435/4; 435/6; 435/69.1; 435/70.1

[58] Field of Search .................... 435/6, 69.1, 70.1, 4, 435/7.2; 514/2

[56] References Cited

U.S. PATENT DOCUMENTS 4,950,591 8/1990 Cherksey .................................. 435/7

OTHER PUBLICATIONS

Vassilev, P. M., T. Scheuer, and W. A. Catterall. Identification of an intracellular peptide segment involved in sodium channel inactivation. *Science Wash. DC* 241:1658-1661, 1988.

(List continued on next page.)

*Primary Examiner*—Margaret Parr
*Assistant Examiner*—Kenneth R. Horlick
*Attorney, Agent, or Firm*—Christensen, O'Connor, Johnson & Kindness

[57] ABSTRACT

Assay for identifying an inactivation gate inhibitor of a sodium channel, by: establishing first and a second cultures of cells having a wild-type sodium channel and third and a fourth cultures of cells having a noninactivating mutant sodium channel; measuring a baseline sodium current for one or more cells in the first and the second cultures, and a baseline inactivation rate for one or more cells in the third and the fourth cultures; treating the cells in the first and the third cultures with either a candidate inhibitor or an IFM amide control, and the cells in the second and the fourth cultures with an inactive control peptide; measuring a test sodium current in one or more cells in the first and the second cultures, and a test inactivation rate in one or more cells in the third and the fourth cultures; and determining that the candidate inhibitor is an inactivation gate inhibitor of the sodium channel if the test sodium current of the cells in the first culture is lower than the baseline of the first culture, the test sodium current of the cells in the second culture is about equal to the baseline of the second culture, the test inactivation rate of the cells in the third culture is higher than the baseline of the third culture, the test inactivation rate of the cells in the fourth culture is about equal to the baseline of the fourth culture, and the candidate inhibitor restores sodium channel inactivation in cells of the third culture to an extent at least equal to the IFM amide control. The candidate inhibitor comprises:

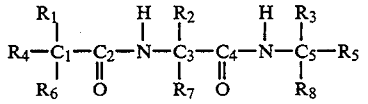

(I)

wherein $R_1$ is straight or branched chain alkyl having a neutral charge; $R_2$ comprises an aryl group; $R_3$ is a straight or branched chain thio-alkyl or alkyl chain having a neutral charge; either $R_4$ or $R_5$ or both are positively charged groups; and $R_6$, $R_7$, and $R_8$ are hydrogen atoms.

1 Claim, 8 Drawing Sheets

OTHER PUBLICATIONS

Vassilev, P. M., T. Scheuer, and W. A. Catterall. Inhibition of inactivation of single sodium channels by a site–directed antibody. *Proc. natl. Acad. Sci.* USA 86:8147–8151, 1989.

Stühmer, W. F. Conti, H. Suzuki, X. Wang, M. Noda, N. Yahadi, H. Kubo, and S. Numa. Structural parts involved in activation and inactivation of the sodium channel. *Nature Lond.* 339:597–603, 1989.

West, J. W., T. Scheuer, L. Maechler, and W. A. Catterall. *Neuron* 8:59–70, 1992, AN.

Margolskee, R. F., B. McHendry–Rinde, and R. Horn. *Soc. for Neurosci. Abst.* 18:644, 1992.

Ukomadu, C., J. Zhou, F. J. Sigworth and W. S. Agnew. *Neuron* 8:663–676, 1992.

Catterall, W. A. Cellular and molecular biology of voltage–gated sodium channels. *Physiol. Reviews* 72:S15–S48, 1992.

West, J. W., D. E. Patton, T. Scheuer, Y. Wang, A. L. Goldin, and W. A. Catterall. A Cluster of hydrophobic amino acid residues required for fast $Na^+$–channel inactivation. *Proc. Natl. Acad. Sci. USA* 89:10910–10914, 1992.

Patton, D. E., J. W. West, W. A. Catterall, and A. L. Goldin. Amino acid residues reuired for fast $Na^+$–channel inactivation: Charge neutralizations and deletions in the III–IV linker. *Proc. Natl. Acad. Sci. USA* 89:10905–10909, 1992.

Brussard, A. B., J. C. Lodder, A. Ter Maat, T. A. de Vlieger, and K. S. Kits. Inhibitory modulation by FMRFamide of the voltage–gated sodium current in identified neurones in *Lymnaea stagnalis. J. Physiol.* 441:385–404, 1991.

Toro, L., E. Stefani, and R. Latorre. Internal blockade of a $Ca^{2+}$–activated $K^+$ channel by shaker B inactivating "ball" peptide. *Neuron* 9:237–245, 1992.

METHODS OF IDENTIFYING SPECIFIC INACTIVATION GATE INHIBITORS OF THE SODIUM CHANNEL

This invention was made with government support under grant 5-RO1NS15751 awarded by the National Institutes of Health. The government has certain rights in this invention.

FIELD OF THE INVENTION

The invention relates generally to molecular biology, and particularly to inhibitors of the sodium ion channel.

BACKGROUND OF THE INVENTION

The voltage-sensitive sodium channel is responsible for the electrochemical action potential in nerve, neuroendocrine, skeletal muscle, and heart cells. The action potential is generated by a rapid increase in sodium permeability. Electrically excitable cells maintain a high intracellular K+ concentration and a low intracellular Na+ concentration (relative to the extracellular fluid) by energy-dependent cation pumping mediated by Na+-K+-ATPases. The resting membrane potential (inside negative) is maintained in excitable cells by surface membranes that are specifically permeable to K+. During generation of an axonal action potential, voltage-sensitive ion channels respond with large increases in permeabilities to specific ions on a time scale of milliseconds. Estimates imply physiological ion transport rates of $>10^7$ ions per second, consistent with the movement of Na+ through a fixed pore or channel. The depolarizing phase of the action potential results from an increase in sodium permeability, whereas repolarization and hyperpolarization following the action potential result from increases in potassium permeability. Sodium permeability changes during depolarization are biphasic with first a dramatic increase and then a decrease to the baseline level after ~1 ms. Thus, the sodium channel fulfills fundamentally different functions in cells than the potassium channel, and the electrochemical events mediated by the two channels are diametrically opposed but balanced.

It has been suggested that sodium channel "activation" controls the rate and voltage dependence of the sodium permeability increase during depolarization, while "inactivation" controls the rate and voltage dependence for the return to resting levels during a maintained depolarization. The sodium channel therefore appears to exist in three functionally distinct states or groups of states: resting, active, and inactivated. Both resting and inactivated states do not conduct ions, and channels that have been inactivated by prolonged depolarization are refractory unless the cell is electrically repolarized to allow them to return to the resting state. The rapid ion conductance by the sodium channel is remarkably selective, with potassium being only ~8% as permeable as sodium, and rubidium and cesium even less permeant (1; see the appended Citations). These fundamental electrochemical properties of sodium channels are the foundation on which essentially all subsequent studies of sodium channel function have been based.

On theoretical grounds, the changes in sodium channel permeability during activation most likely result from conformational changes in one or more channel components. One or more membrane proteins may be induced to undergo a voltage-driven change in conformation to a new stable state in which the net charge, or the location of charge, within the membrane electrical field has been altered. A movement of membrane-bound charge can give rise to a measurable capacitive current detected as "gating currents" (2, 3) by using electrophysiological methods. Inactivation of sodium channels blocks gating currents.

Identification of sodium channel polypeptides was achieved by covalent in situ labeling of a neurotoxin receptor site 3 using a photoreactive azidonitrobenzoyl derivative of scorpion toxin (4). Two polypeptides of 260 kDa and 36 kDa were identified by SDS-PAGE that have subsequently been termed the α- and β1-subunits. In contrast, the Triton X-100 solubilized sodium channel from rat brain reportedly has a Stokes radius of 80 Å, a sedimentation coefficient of 12 S, a partial specific volume of 0.82 $cm^3/g$ (5), and a deduced molecular mass of about 601 kDa (i.e., for the protein-detergent complex). The purified rat brain sodium channel consists of three polypeptides: α of 260 kDa, β1 of 36 kDa, and β2 of 33 leda (6, 7, 8, 9). β2 is covalently attached to α by disulfide bonds, and β, is associated noncovalently (8, 9) The subunits appear to be present in a 1:1:1 stoichiometry (7), and all three polypeptides are intrinsic membrane glycoproteins.

Nucleotide sequences encoding a sodium channel polypeptide were reported for an electric eel electroplax sodium channel (10). The deduced amino acid sequence revealed a protein with four internally homologous domains, each containing multiple potential α-helical transmembrane segments. The cDNAs encoding the electroplax sodium channel were used to isolate other cDNAs encoding three distinct, but highly homologous, rat brain sodium channels (types I, II, and III; 11, 12). The type II gene contains two adjacent exons that are alternatively spliced into mature mRNA in a developmentally regulated manner. The type II sodium channel is most prominent in embryonic and neonatal brain, whereas the type IIA channel is most prominent in the adult brain (13, 14). Each of these sodium channel α-subunits consists of four homologous domains. cDNAs encoding the alternatively spliced rat brain type IIA sodium channel α-subunit have been isolated (15, 16), and the type II/IIA cDNA was used as a probe at low stringency to isolate cDNAs encoding sodium channel α-subunits expressed in skeletal muscle and heart (17, 18, 19). The μ-sodium channel α-subunit is expressed primarily in adult skeletal muscle (19); the h1 sodium channel α-subunit is expressed primarily in heart and also in uninnervated or denervated skeletal muscle (17, 18). These sodium channels have the alpha helical transmembrane structural motifs similar to those in the α-subunits of the brain sodium channel.

The inactivation gate, which closes the sodium channel during prolonged depolarization, is formed by the intracellular protein segment connecting homologous domains III and IV. Antibodies against this segment prevent inactivation and therefore keep the channel open during prolonged depolarization (20, 21). Mutations which cut the protein between domains III and IV also slow inactivation (22). This segment serves to close the channel.

SUMMARY OF THE INVENTION

A family of synthetic peptides which are modeled on the structure of the inactivation gate is disclosed that are capable of inhibiting voltage-gated sodium channels in cells. One such peptide, with an amino acid sequence IFM (isoleucine- phenylalanine-methionine; SEQ. ID No: 1) interacts with a specific inactivation gate receptor in the interior cytoplasmic portion of the sodium channel and blocks the channel. Trimeric IFM-amide derivatives were found to insert between an open inactivation gate and its receptor and block the action of the inactivation gate by binding to the receptor. The invention is directed to sodium channel inactivation gate peptides comprising a compound of formula I and pharmaceutically acceptable salts thereof:

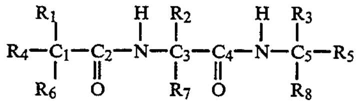

(I)

wherein: $R_1$ is straight or branched chain alkyl having a neutral charge, preferably sec-butyl; $R_2$ comprises an aryl group and is preferably benzyl; $R_3$ is a straight or branched chain thio-alkyl, preferably methylthiobutyryl-, or alkyl chain having a neutral charge; either $R_4$ or $R_5$ or both are positively charged groups; and $R_6$, $R_7$, and $R_8$ are preferably hydrogen atoms. $R_4$ is preferably an amine group; and $R_5$ is preferably an amido group.

The invention also provides an assay for identifying inactivation gate inhibitors of the sodium channel. First, cultures are established of a cell line (e.g., F1489Q) having a sodium channel with a mutation that renders the inactivation gate nonfunctional. The cells in one culture are treated with a candidate inactivation gate inhibitor and the cells in a second culture with an inactive peptide (e.g., KIQMK; SEQ. ID. NO. 2). The rate of inactivation of the sodium channel is measured in one or more cells in each of the first and the second cultures. If the sodium channel inactivation is restored in the cells in the first culture but not in the cells in the second culture, the candidate inactivation gate inhibitor is considered to be capable of inhibiting a sodium channel as the inactivation gate does in the cell. The inhibitor preferably restores inactivation and blocks the cycling of the sodium channel to an extent at least equal to IMF amide. In parallel, effects of the candidate inactivation gate inhibitors are also tested on wild-type sodium channels expressed in a cell line (e.g., CNaIIA-1 cells) to confirm that wild-type sodium channels are blocked.

BRIEF DESCRIPTION OF THE DRAWINGS

FIG. 2A shows an insignificant level of inhibition of sodium channel inactivation within 4 minutes of cycling in the presence of KIFMK (−KIFMK) relative to a control recording in the absence of KIFMK (-KIFMK). FIG. 2B shows a substantial level of inhibition after 15 minutes of cycling the sodium channels. FIG. 2C shows the square voltage pulse applied to depolarize the cells and produce the effects seen in FIGS. 2A and 2B.

FIG. 5A shows sodium currents in patch clamped CNaIIa-I cells with no peptides added. FIG. 5B shows significant tail currents (arrows) generated by KIFMK as it inhibits closure of the inactivation gate of the sodium channel in CNaIIa-I cells. FIG. 5C shows no significant gating currents generated by mutant KIQMK peptides. FIG. 5D shows the square wave voltage potentials applied to the cells in FIGS. 5A, 5B, and 5C.

DETAILED DESCRIPTION OF THE PREFERRED EMBODIMENT

Figure 1:
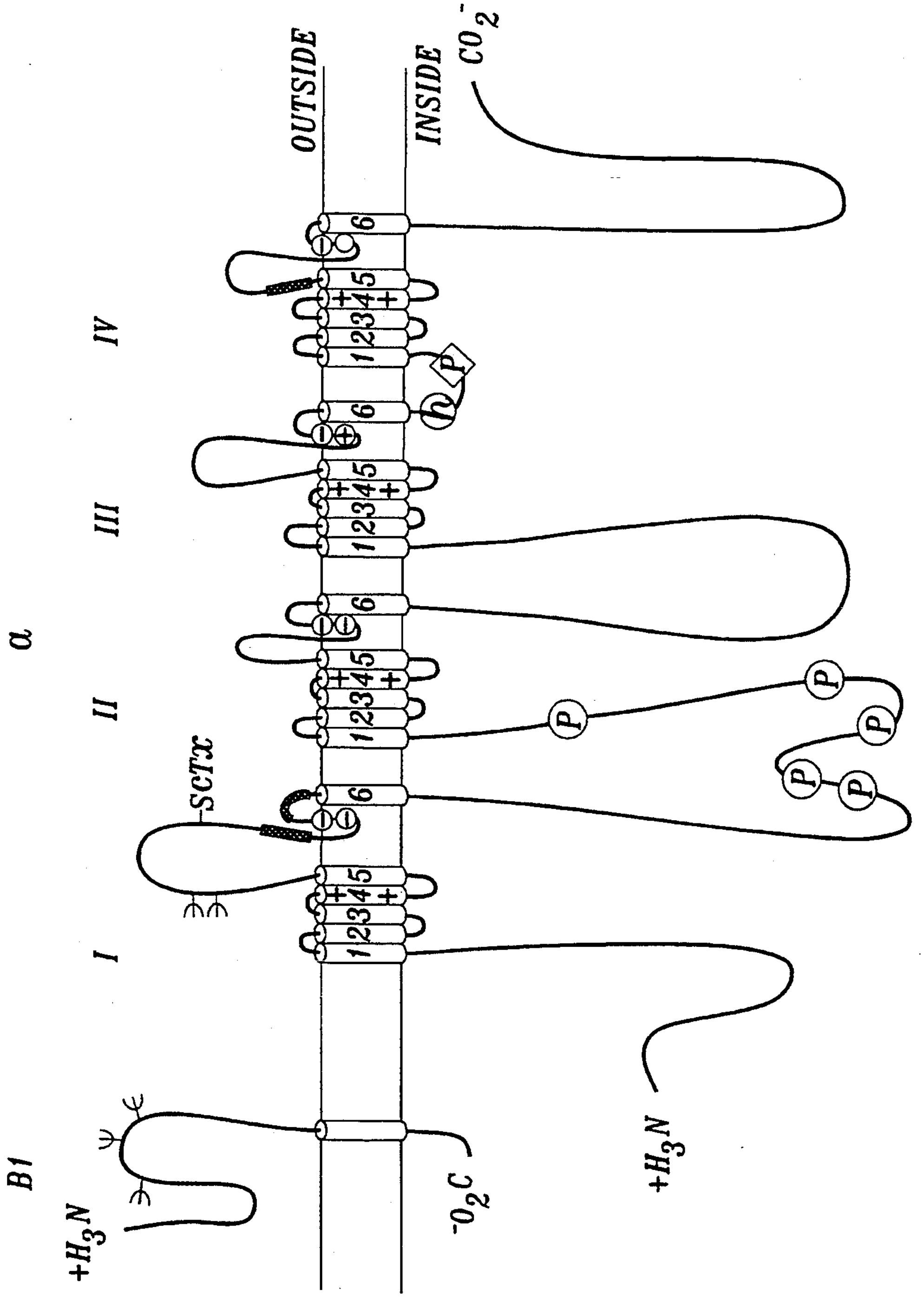
FIG. 1 illustrates primary structures of α- and β1-subunits of a representative sodium channel. Bold line, polypeptide chains of α- and β1-subunits with length of each segment approximately proportional to its true length in rat brain sodium channel. Cylinders represent probable transmembrane α-helices. Other probable membrane associated segments are drawn as loops in extended conformation like remainder of sequence. Also shown are sites of experimentally demonstrated glycosylation (ψ), cAMP-dependent phosphorylation (P in a circle), protein kinase C phosphorylation (P in a diamond), amino acid residues required for tetrodotoxin binding (small circles with +, −, or open fields depict positively charged [$Lys^{1422}$], negatively charged, or neutral [$Ala^{1714}$] residues, respectively), and amino acid residues that form the inactivation particle (h in a circle).

Inactivation gate inhibitors. Until the experiments disclosed herein were conducted it was not known that: 1) the molecular conformation of the intracellular domain of the sodium channel is sufficiently unrestricted to allow entry of a pentapeptide (i.e., KIFMK) which mimics the inactivation gate structure; 2)the inactivation gate receptor of a rapidly cycling sodium channel is still accessible to a pentapeptide; 3) the inactivation gate of the sodium channel consists of an IFM ligand interacting with a previously unknown inactivation gate receptor; and, 4) an inactivation gate peptide could be successfully interposed between an inactivation gate peptide and its inactivation gate receptor to block the sodium channel.

The following terms used herein are intended to have the meanings set forth below:

The term "sodium channel" is used herein interchangeably with "voltage gated sodium channel" to mean a cell membrane channel that is capable of conducting sodium from the extracellular space into the cytoplasm of a cell in a manner that is dependent upon the electrical potential of the cell membrane. The sodium channel is composed of one or more polypeptides. Each type of sodium channel has an α-subunit with four homologous domains having six alpha helical transmembrane segments. Representative examples of the subject sodium channels may be isolated in the plasma membrane fraction from skeletal muscle, heart, and brain. The purified types I, II, IIA, III, μl, and hl (e.g., as described in citations 4, 6–9, 11–14, and 18–19) are representative sodium channels.

The term "activated sodium channel" is used interchangeably with "open sodium channel" to refer to the state in which the sodium channel is conductive of sodium ions. The activated sodium channel has a conformational state distinct from a "resting" or an "inactivated" state. When the activated sodium channel is in the membrane of an electrically excitable cell, sodium ions are conducted from the exterior of the cell to the cytoplasm in response to a change in membrane potential. "Membrane potential" refers to the voltage difference across the cell membrane. Changes in membrane ionic currents of electrically excitable cells in response to changes in membrane potential may be measured according to methods illustrated in the Examples below. Ionic currents associated with activation of the sodium channel may be measured using methods that are also illustrated in the Examples. A representative example of a sodium channel was constructed by stably transfecting a Chinese Hamster Ovary (CHO) cell with a cDNA encoding a sodium channel and isolating the cell line CNaIIA-1. These sodium channels were activated by applying a membrane depolarizing voltage pulse to the cell membrane (e.g., −50 to +100 mV).

The term "closed sodium channel" is used to denote the state in which the sodium channel is not conductive of sodium ions but can be activated (opened) by depolarization.

The term "inactivated sodium channel" is used to denote the state in which the sodium channel is not conductive of sodium ions and cannot be activated by depolarization. The inactivated sodium channel has a conformational state distinct from a "resting" or an "activated" state. When the inactivated sodium channel is in the membrane of an electrically excitable cell, sodium ions are not conducted from the exterior of the cell to the cytoplasm in response to a change in membrane potential. Representative examples of inactivated sodium channels are found in electrically-excitable cells (i.e., having voltage gated sodium channels), after the cells have been exposed to prolonged or repeated membrane depolarizing events, such as a change in the cell membrane electrical potential induced by an applied voltage. A representative example of an inactivated sodium channel was established by applying prolonged (>10 msec) or repetitive voltage pulses to the cell membrane (e.g., −50 to +100 mV at 10 Hz) of a CNaIIA-1 cell.

The term "cycling" is used to refer to a process of repetitively depolarizing a cell membrane containing a sodium channel (i.e., so that the sodium channel repetitively changes from a closed state to an open or inactivated state), with sufficient time being allowed for repolarization of the membrane before the next depolarizing event. Cycling of sodium channels may conveniently be measured as changes in cell membrane ionic currents as the sodium channel opens and closes, as illustrated in the Examples. The rate at which a sodium channel is inactivated can also be measured by a variety of means, and is termed herein the "rate of inactivation." For example, a prolonged (>10 msec) voltage pulse may be applied to a cell membrane at given frequency (e.g., −50 to +100 mV at 10 Hz). The status of the sodium channel (i.e., open or closed) may be monitored by measuring the electrical current caused by sodium ion movement through the channel, i.e., the sodium current. Sodium current may conveniently be measured with time as described in the Examples, below. Using sodium current measurement, the rate of inactivation is the rate at which the sodium current across the membrane during depolarization drops to a baseline value.

The term "noninactivating mutant sodium channel" is used to refer to a genetically altered sodium channel which, when located in a cell membrane, conducts sodium ions under membrane depolarizing conditions that would produce inactivation in a wild-type sodium channel. Noninactivating mutant sodium channels may conveniently be identified as sodium channels that have a rate of inactivation that is slower than a wild-type sodium channel. In a representative example, the noninactivating F1489Q mutant sodium channel as transiently expressed in TSQ-201 cells is completely (or partially) resistant to application of a prolonged (>10 msec) voltage pulse. Since the sodium channel remains open to passage of sodium ions, a sodium current can be measured under membrane depolarizing conditions that would normally inactivate a wild-type sodium channel.

The term "inactivation gate peptide" is used interchangeably with "gate peptide" herein to mean a member of a family of peptides modeled on the structure of the inactivation gate which are capable of specifically blocking a cycling sodium channel and not a resting (closed) sodium channel. A representative inactivation gate peptide has the following structure:

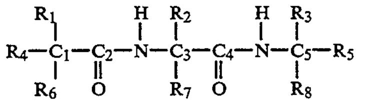

(I)

wherein: $R_1$ is straight or branched chain alkyl having a net negative or neutral charge, preferably sec-butyl; $R_2$ comprises an aryl group and is preferably benzyl; $R_3$ is a straight or branched chain thio-alkyl, preferably methylthiobutyryl-, or alkyl chain having a net negative or neutral charge; either $R_4$ or $R_5$ or both are positively charged groups; and $R_6$, $R_7$, and $R_8$ are preferably hydrogen atoms. $R_4$ is preferably an amine group; and $R_5$ is preferably an amido group.

The preferred inactivation gate peptides are chemically modified and derivatized tri-, tetra-, and pentapeptides containing the core sequence IFM. IFM amide is presently the most preferred derivative peptide.

It will be understood that closely related analogs of isoleucine may be useful in the inactivation gate peptides of the invention. For example, aliphatic $R_1$ groups such as methyl- (Ala), ethyl-, propyl, isopropyl- (Val), butyl- (Abu), and sec-butyl- (Ileu) may be useful. Other phenyl-derivatives ($R_2$) are also contemplated, particularly $R_2$ groups substituted with groups designed to disperse the $\delta^-$ charge of the ting and/or increase the ability of the ting to participate in hydrophobic interactions with the sodium channel inactivation gate receptor. Examples of such substituted phenyl derivatives include Nα-methyl amino acids, e.g., phenyl (Ph), as well as heterocyclic aromatic rings containing N, O, or S. Each carbon ring may be substituted by one to three members independently selected from among, e.g., $C_1$–$C_7$ alkyl, amino (Am), mono- or di-$C_1$–$C_4$ alkylamino, phenyl-$C_1$–$C_4$ alkyl, amino-$C_1$–$C_4$ alkyl, hydroxylic $C_1$–$C_4$ alkyl, mono- or di-$C_1$–$C_4$ alkylamino-$C_1$–$C_4$-alkyl, hydroxyl, guanidyl, guanidyl $C_1$–$C_4$ alkyl, $C_1$–$C_4$ alkoxy, $CF_3$, halo, CHO, $CO_2H$, $CONH_2$, CONH -$C_1$–$C_4$ alkyl, $CON(C_1$–$C_4$ alkyl$)_2$, or CO-$C_1$–$C_4$ alkyl.

$R_4$ may be a positively charge aliphatic residue such as $-CH_2NH_3+$ or alternatively an α-amino group. $R_5$ may be $CONH_2$, the amide of the carboxyl group of the amino acid bearing $R_3$, or another neutral or positively charged group.

The subject inactivation gate peptides all have the properties of: a) inhibiting an activated wild-type sodium channel in a test cell; and, b) restoring sodium channel inactivation to noninactivating mutant sodium channels. The latter properties of the subject peptides may be determined using test cells in a screening assay such as that depicted in a tabular form in Table A, below.

TABLE A

| Culture (#) | Channel (type)* | Baseline Measurement | Treatment | Test Measurement | Inactivation Rate |
|---|---|---|---|---|---|
| 1 | WT | baseline sodium current | candidate inhibitor | test sodium current | test < baseline |
| 2 | WT | baseline sodium current | inactive peptide | test sodium current | test ≅ baseline |
| 3 | NA | baseline inactivation rate | candidate inhibitor | test inactivation rate | test > baseline |
| 4 | NA | baseline inactivation rate | inactive peptide | test inactivation rate | test ≅ baseline |

*WT, wild type sodium channel;
NA, noninactivating mutant sodium channel

Wild-type (WT) and noninactivating (NA) mutant sodium channels may be naturally expressed in the test cells, or the sodium channel may be transfected or transduced into the test cells. The subject screening assay may conveniently employ two different cell types, i.e., a first cell type expressing the wild-type sodium channel and a second cell type expressing the mutant sodium channel. In the first step, baseline measurements of the sodium channel activation and inactivation are taken for each type of cell (e.g., as outlined in Table A).

The baseline sodium current rate is determined by whole cell voltage clamp recording in one or more cells in a culture as a function of time following membrane depolarization.

The baseline inactivation rate is determined in each cell type by recording the time course of decay of the sodium current in response to a membrane depolafizing agent.

Both cell types have similar baseline activation rates, but differ in their inactivation rates where the cell having the wild-type sodium channel exhibits a rate of inactivation that is faster than cell having the noninactivating mutant sodium channel.

Next, a candidate compound of formula I is introduced into both test cells, e.g., by microinjection, addition to the medium, or introduction through a recording microcapillary pipet. For the cells having the wild-type sodium channel (e.g., Cultures #1-#2, Table A), the level of sodium current is determined; and, for the cells having the noninactivating mutant sodium channel the sodium channel inactivation rate is determined (e.g., Cultures #3-#4, Table A). In both cases the response of the treated test cells is determined by exposure to the same membrane depolarizing stimulus as that used in constructing the baseline responses (i.e., above). Next, the sodium current resulting from the depolarization is recorded; and the effect of the test agent is identified as the difference between the respective test rate and baseline activation or inactivation rate. A comparison of the baseline recording with the recording made in the presence of the candidate compound indicates: a) whether inhibition of activation has occurred in the wild-type cell, and b) whether the noninactivating mutant sodium channel now exhibits properties of an inactivation response, i.e., whether the inactivation response has been restored in the mutant. Of course, inhibition or restoration may be partial or complete and the extent may be quantified as a fractional value or fold-increase over the baseline measurement. In the test assay illustrated in Table A, above, the subject inactivation gate peptides all have the properties of: a) inhibiting an activated wild-type sodium channel in a test cell, i.e., inhibiting the wild-type activation response so that the sodium current of cells in Culture #1 is decreased relative to baseline; and, b) restoring sodium channel inactivation to noninactivating mutant sodium channels, i.e., restoring an inactivation response in the mutant so that the test inactivation rate of cells in Culture #3 is increased relative to baseline. Skilled artisans will of course recognize that restoration of an inactivation response by a candidate compound in a noninactivating mutant may be a matter of degree, and that having a control to account for changes in the buffer and assay conditions may be advantageous, e.g., Cultures #2 and #4, Table A. For instance, a known inactive agent, such as a peptide that does not have the structure of formula I, may be used as a control by adding it in place of the candidate compound to each type of test cells. In the latter case, the test activation and inactivation rates for the cells in Cultures #2 and #4, respectively, should remain about the same as the baseline measurements for the assay to be valid.

Illustrative screening assays are provided in Examples 1–6 below, for measuring the activation of sodium currents and inactivation responses of sodium channels in wild-type sodium channels as well as in noninactivating sodium channels. Examples are also provided for determining that a peptide agent of formula I inhibits the response of an activated sodium channels and restores the response of a defective inactivation mutant sodium channel.

As used herein, "aryl" is intended to mean a compound with one or more cyclic aromatic carbon rings, e.g., phenyl (Ph), as well as heterocyclic aromatic rings containing N, S, or O, e.g., naphthyl-, anthracyl-, phenanthryl-, pyridyl-, pyrimidyl-, quinolyl-, isoquinolyl-, glycosyl-, glycol, and epoxide.

Synthesis. The preparation of the subject inactivation gate peptides and derivatives thereof is carried out according to methods well known in the peptide synthesis field, using either liquid or solid phase techniques. According to liquid phase methods, the exemplary three amino acids (i.e., Ile, Phe, and Met, or their derivatives or analogs) are stepwise condensed to form the peptide bonds, i.e., the $C_2$-NH and $C_5$-NH peptide bonds. The condensations are accomplished using a suitable solvent such as DMF (N,N-dimethylformamide), THF (tetrahydrofuran), or chlorinated solvent. The $C_1$–$C_5$ chain of formula I is formed starting from either the N-terminal or the C-terminal amino acid, wherein the carboxy group is first suitably protected, e.g., as ester. The amino groups of the amino acids (which must not be involved by the two subsequent condensation steps) are rendered nonreactive by protecting groups such as, e.g., terbutyloxycarbonyl (Boc), benzyloxycarbonyl (Z), fluorenylmethoxycarbonyl (FMOC), triphenylmethyl, tosyl, formyl, phthaloyl groups, etc. The protecting groups are selectively removed as required in the synthesis, and according to methods specific for the different protective groups as is known in the art. For avoiding undesired side reactions, when the compounds of general formula I have free —OH and/or —COOH groups, such groups are preferably protected (in the respective starting amino acids) using protective groups that are subsequently removed after formation of the $C_1$–$C_5$ chain. Hydroxy groups are protected by esterification or etherification (particularly benzyl-etherification), and the carboxy groups by esterification with alcohols (particularly benzyl alcohol). If the final products of general formula I have substituted hydroxy and/or carboxy groups, the respective substitutions are preferably inserted in the corresponding amino acid before the peptide chain formation, so that further protective groups are not required. However, it is also possible to substitute the final product (I) by addition of free hydroxy and/or carboxy groups.

Peptide bond formation occurs according to methods known in the art such as, e.g., by reacting the amino group with a mixed anhydride, which is prepared in situ by employing an alkyl (e.g., ethyl or isobutyl) chlorocarbonate, or by reacting the amino group with an active derivative of the carboxyl such as, e.g., an acyl chloride, a N-hydroxysuccinimide ester, a mono- or di-nitrophenyl or penta-halophenyl ester, or with an imidazolide prepared from carbonyldiimidazole. In another method the peptide bond is formed directly between an amino group and a carboxy group using a carbodiimide as a coupling reagent (e.g., dicyclohexylcarbodiimide; DCC) in the optional presence of agents such as N-hydroxybenzotriazole (HOBT) or dimethylaminopyridine (DMAP). The reactions are commonly carried out in THF, DMF, or chlorinated solvents, at temperatures ranging from $-20°$ C. and $60°$ C., and preferably between $4°$ C. and $30°$ C.

Alternatively, the formula I compounds are prepared by means of sequential reactions using solid phase peptide synthesis (Merrifield method). One route of synthesis involves esterification of a styrene-divinylbenzene chloromethylated copolymer (Merrifield resin, 1% cross-linked) with the carboxy-terminal amino acid having a protective group for the amino group (e.g., Boc). After isolating the Boc-protected amino acid resin compound and determining the degree of esterification (mmol of amino acid/g of resin), the N-protecting group is removed according to known methods, e.g., by reaction with trifluoroacetic acid. After treating with triethylamine, the condensation of the next amino acid is initiated. In this case, the N-terminal amino acid is blocked (e.g., as N-Boc) and other protective groups are used to block any phenolic hydroxy groups of the $R_2$ side-chain (e.g., as benzylesters or benzylethers) suitably protected. The second condensation reaction is sequentially carried out according to one of the same procedures described above for peptide bond formation, e.g., condensation with DCC. The O-benzyl-protected N-Boc-tripeptide-resin compound is so obtained. The cleavage from the resin and the N,O-deprotections are carried out according to known methods such as treatment with gaseous HBr in TFA in the presence of anisole, or with liquid dry HF. After the deprotonation of the amino group by means of a base and suitable isolation and purification steps, the product of formula I is obtained as white powder. Optional substituents at amino and/or hydroxy and carboxy groups are added, according to the general formula I, as substituents of the relevant amino acids before beginning the peptide condensation reactions described above, or such substituents can be added after the $C_1$–$C_5$ peptide chain has been formed.

Formulation. Salts of formula I may be prepared at $R_4$ when $R_4$ is positively charged, e.g., an amine, or at $R_5$ when $R_5$ is negatively charged, e.g., a carboxy. Salts at such exemplary $R_4$ or $R_5$ are prepared by treating with equivalent amounts of acids or bases, respectively, in aqueous or organic solution. The salts are obtained from the solutions thereof by concentrating and/or cooling, evaporation to dryness, freeze-drying, spray-drying, precipitation by solvents, etc.

Pharmaceutically acceptable salts of the subject inactivation gate peptides (I), e.g., in the form of water- or oil-soluble or dispersible products, include nontoxic salts or quaternary ammonium salts of the compounds (I) that are formed with inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

Therapeutic uses. The inactivation gate compounds (I) are potentially useful as antiarrhythmic, anticonvulsant, local anesthetic, analgesic, and neuroprotective drugs.

As antiarrhythmic drugs, the inactivation gate compounds (I) are used to treat arrhythmias of the atria or ventricles of the heart in which abnormally rapid cardiac action potentials occur in either chamber or premature action potentials occur in the ventricles. Representative clinical disorders that can potentially be treated by these compounds include atrial tachycardia, atrial flutter and fibrillation, atrial arrhythmias due to reentry, Woolf-Parkinson-White syndrome, ventricular premature systole (also called premature ventricular contractions, PVCs), ventricular tachycardia and fibrillation, and sudden cardiac death. Antiarrhythmic drugs may also be administered to patients following a myocardial infarction ("heart attack") or to patients with congestire heart failure or cardiomyopathy in order to prevent arrhythmias. Desired clinical end points for treatment of these disorders include reduction of heart rate, regularization of ventricular rhythms, prevention of premature ventricular systoles, and prevention of ventricular fibrillation and sudden cardiac death. The efficacy of the subject compounds (I) in treatment of arrhythmias is first established in animal models of cardiac arrhythmia including arrhythmias initiated by electrical stimulation, focal myocardial injury, and ischemic injury followed by electrical stimulation or coronary arterial occlusion.

As anticonvulsant drugs, the inactivation gate compounds (I) and their derivatives are used to treat epileptic seizures including grand mal, temporal lobe, and partial complex seizures. Desired clinical end points include reduction of frequency and severity of seizures. Efficacy is demonstrated in animal models of seizure including maximal electroshock seizures, seizures due to kainic acid lesions of the hippocampus, seizures due to "kindling" of the amygdala in rat, and seizures induced by topical alumina cream on the cortical surface of monkeys.

As local anesthetic drugs and analgesics, the inactivation gate compounds (I) and derivatives are used to provide relief from pain in dentistry and localized surgical and medical procedures. They may be administered by localized injection or by intrathecal or epidural infusion. These therapeutic applications would be tested by measurement of block of sensory nerve conduction by the inactivation gate compounds, and by block of pain responses, using standard small animal tests of pain transmission including the hot plate and tail flick tests, the induction of neuromas by surgical section of peripheral nerves, and the induction of pain by cutaneous pressure.

As neuroprotective agents, the inactivation gate compounds (I) are used to prevent neuronal damage and death during and follow ischemic episodes associated with cardiac surgery, cerebral aneurysm, and stroke. Therapeutic value is assessed from retention and recovery of normal neurological status following stroke. Efficacy in neuroprotection is assessed in animal models of stroke involving experimental occlusion of major cerebral arteries such as the middle cerebral artery occlusion model.

Administration. For purposes of administering a therapy to a patient in need thereof, the subject inactivation gate compounds (I) may be administered orally or parenterally, in dosage unit formulations containing conventional nontoxic, pharmaceutically acceptable carders, adjuvants, and vehicles. The term "parenteral" as used herein includes subcutaneous injections, intravenous, intramuscular, intrastemal injection, or infusion techniques. Intrathecal infusion and injection are additional modes of administration in special circumstances.

Liquid form preparations include solutions, suspensions, and emulsions. As an example may be mentioned water or water/propylene glycol solutions for parenteral injection. Liquid preparations can also be formulated in solution in aqueous polyethyleneglycol solution. Aqueous suspensions suitable for oral use can be made by dispersing the finely divided active component in water with viscous material, e.g., natural or synthetic gums, resins, methylcellulose, sodium carboxymethylcellulose, and other well-known suspending agents.

Also included are solid form preparations that are intended to be converted shortly before use to liquid form preparations for either oral or parenteral administration. Such liquid forms include solutions, suspensions, and emulsions. These particular solid form preparations are most conveniently provided in unit dosage form and as such are used to provide a single liquid dosage unit. Alternately, sufficient solid compound (I) may be provided so that, after conversion to liquid form, multiple individual liquid doses may be obtained by measuring predetermined volumes of the liquid form preparation as with a syringe, teaspoon, or other volumetric container.

The injectable solutions or suspensions may be formulated according to known techniques, using suitable nontoxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When administered orally as a suspension, these compositions (particularly the peptide derivatives) may contain microcrystalline cellulose for imparting bulk, alginic acid or sodium alginate as a suspending agent, methylcellulose as a viscosity enhancer, and sweeteners/flavoring agents known in the art. As immediate-release tablets, these compositions may contain microcrystalline cellulose, dicalcium phosphate, starch, magnesium stearate and lactose and/or other excipients, binders, extenders, disintegrants, diluents, and lubricants known in the art.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampules. The unit dosage form can also be a capsule, cachet, or tablet itself, or it can be the appropriate number of any of these in packaged form. The quantity of active compound in a unit dose of preparation may be varied or adjusted according to the particular application and the potency of the active ingredient. The compositions can, if desired, also contain other compatible therapeutic agents.

In therapeutic use as a sodium channel inhibitor, the dosage range may be varied depending upon the requirements of the patient, the severity of the condition being treated, and the particular compound (I) being employed. Determination of the proper dosage for a particular situation is within the skill of the art. Generally, treatment is initiated with small dosages that are less than the optimum dose of the compound. Thereafter the dosage is increased by small increments until the optimum effect under the circumstances is reached. For convenience, the total daily dosage may be divided and administered in portions during the day if desired.

EXAMPLE 1

Voltage- and frequency-dependent block of sodium channels.

Experiments were performed on wild-type Type IIA sodium channels stably transfected into Chinese hamster ovary (CHO) cells (CNaIIA-1; as described in citation 23, which is incorporated herein by reference) and mutant (F1489Q) sodium channels transiently transfected into human kidney carcinoma cells (as described in citations 24 and 25, which are incorporated herein by reference).

Figure 2A:
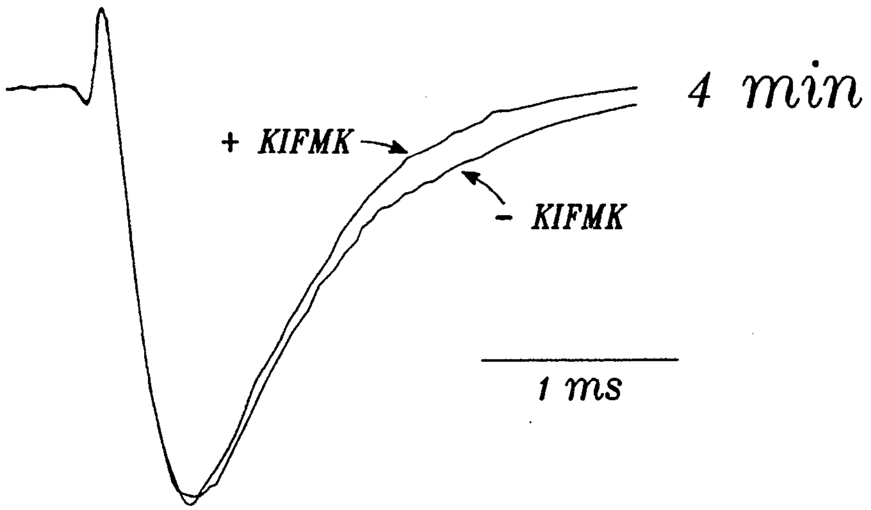
FIGS. 2A–2C shows the results of experiments (described in Example 1) in which inactivation gate peptide KIFMK (SEQ. ID. No. 3) was shown to have a specific inhibitory effect on sodium currents through voltage-activated wild-type IIA sodium channels in stably transfected Chinese hamster ovary (CHO) cells.
Figure 2B:
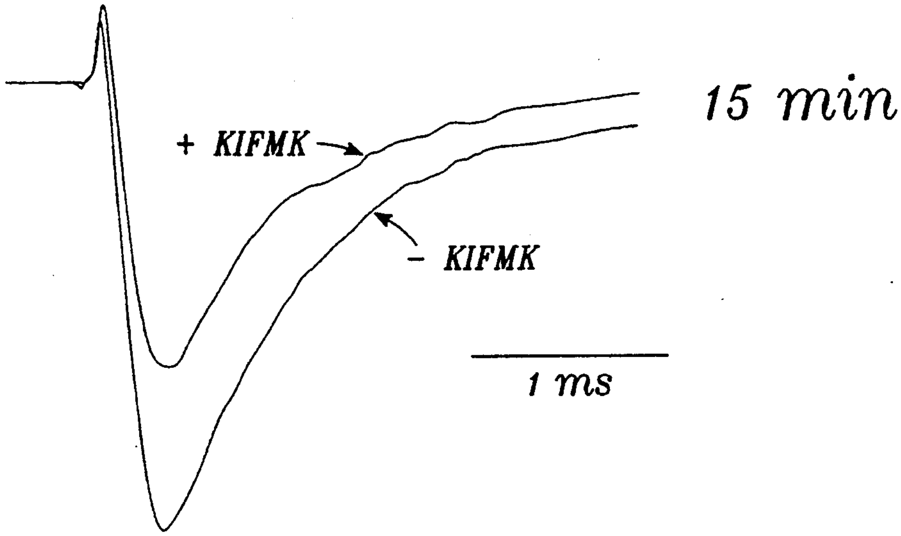
Figure 2C:
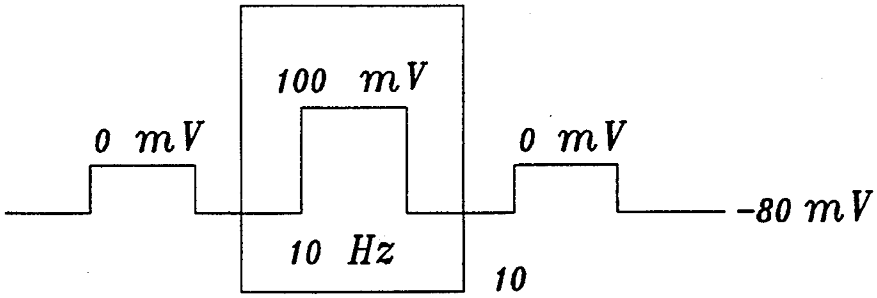
Figure 3:
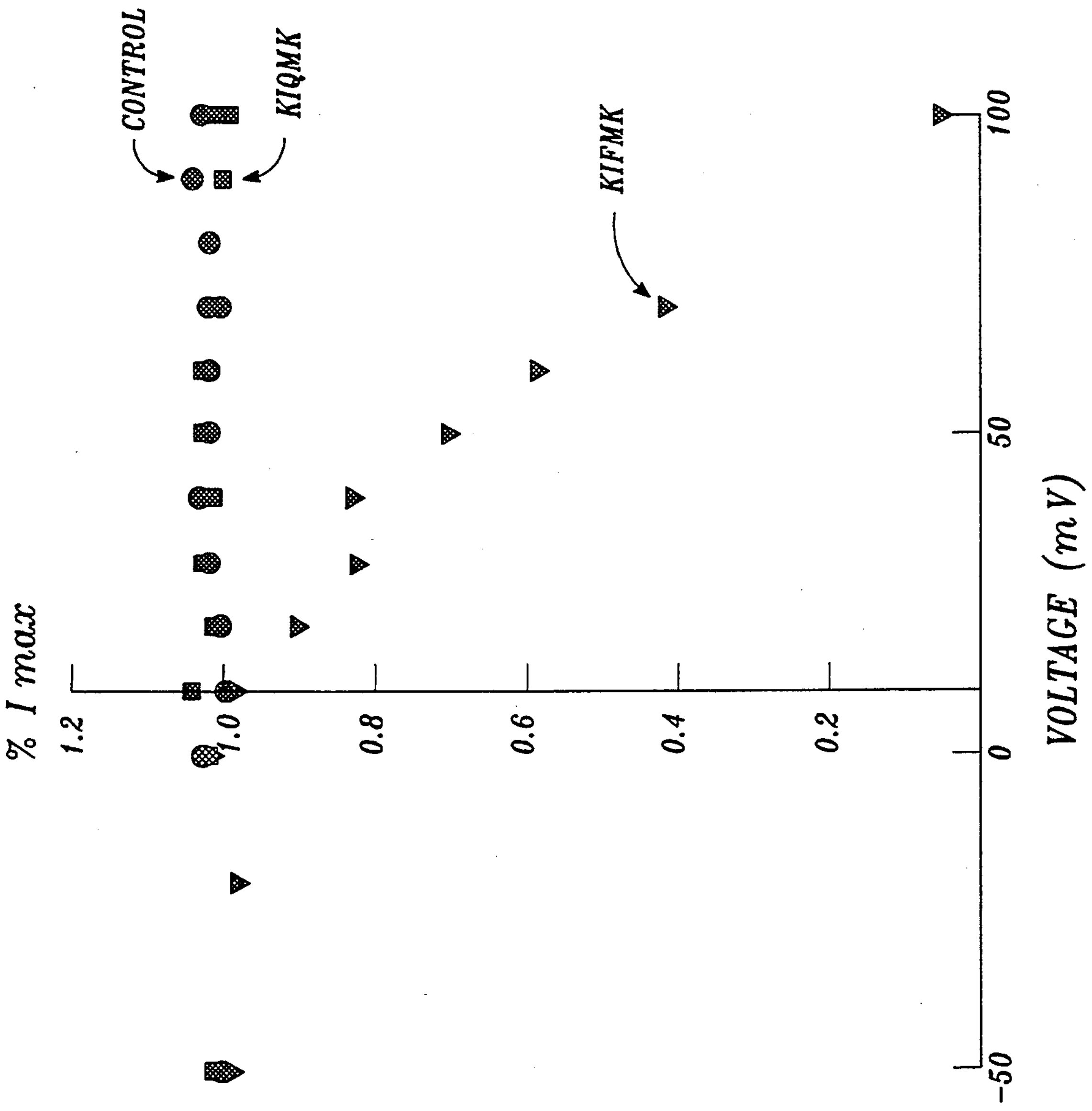
FIG. 3 shows the results of experiments (described in Example 1) in which the inactivation gate peptide KIFMK (KIFMK) inhibited rapidly cycling type IIA sodium channels (filled triangles), even though these channels were normally resistant to inactivation by repeated voltage pulses (filled circles). Mutant gate peptide KIQMK (KIQMK) was inactive in this assay (filled squares) showing the importance of the aromatic residue (i.e., "F") in the nonmutant KIFMK sequence. Imax is maximum sodium current.

The effects of the KIFMK gate peptide on sodium channels was tested by backfilling an electrode with a recording solution containing 1 mM peptide after loading the tip of the electrode with a buffer of peptide-free solution (i.e., to enhance seal formation when the electrode was inserted into a cell). After forming a high-resistance seal and breaking through the cell membrane, the peptide rapidly diffused into the cell and caused the appearance of tail currents (see below) within 10 minutes. When stabilized, sodium currents were recorded in the cells before and after a series of 10 Hz voltage pulses that varied over the range −50 to +100 mV. Parallel control experiments were conducted in which electrodes were not backfilled with peptides. The magnitude of the sodium currents in the experimental and control preparations were compared. Sodium currents were substantially reduced by KIFMK in response to frequent depolarizing pulses after only 15 min. perfusion of the cell with the peptide (FIG. 2). Little reduction in sodium current was observed if the cell membranes were not depolarized frequently, indicating that KiFMK peptides do not bind to "closed" channels and block them. There was substantial KIFMK blockage of gating currents generated in response to 10 Hz pulses at positive voltages (i.e., greater than 0 mV), and the channels were completely blocked by 10 Hz pulses given at 100 mV (FIG. 3, filled triangles). Type IIA sodium channels in these cells did not exhibit voltage-frequency dependent inactivation at any applied voltage at the test frequency used (FIG. 3, filled circles). Thus, the KIFMK gate peptide also inhibited rapidly cycling sodium channels.

As a control, a KIQMK peptide was prepared to mimic the sequence present in mutant F 1489Q sodium channels. KIQMK did not block the type IIA channel over the entire voltage range even though voltage pulses were applied at 10 Hz to repetitively cycle the sodium channels in these cells (FIG. 3, filled squares).

The combined results show that the inhibitory effect of KIFMK on the sodium channel is strong and voltage- and frequency-dependent, indicating that blocking by the peptide requires channel activation; and there is no appreciable block when the channels are not repetitively cycling between the closed, activated and inactivated states.

EXAMPLE 2

Restoration of inactivation in mutant sodium channels.

Figure 4:
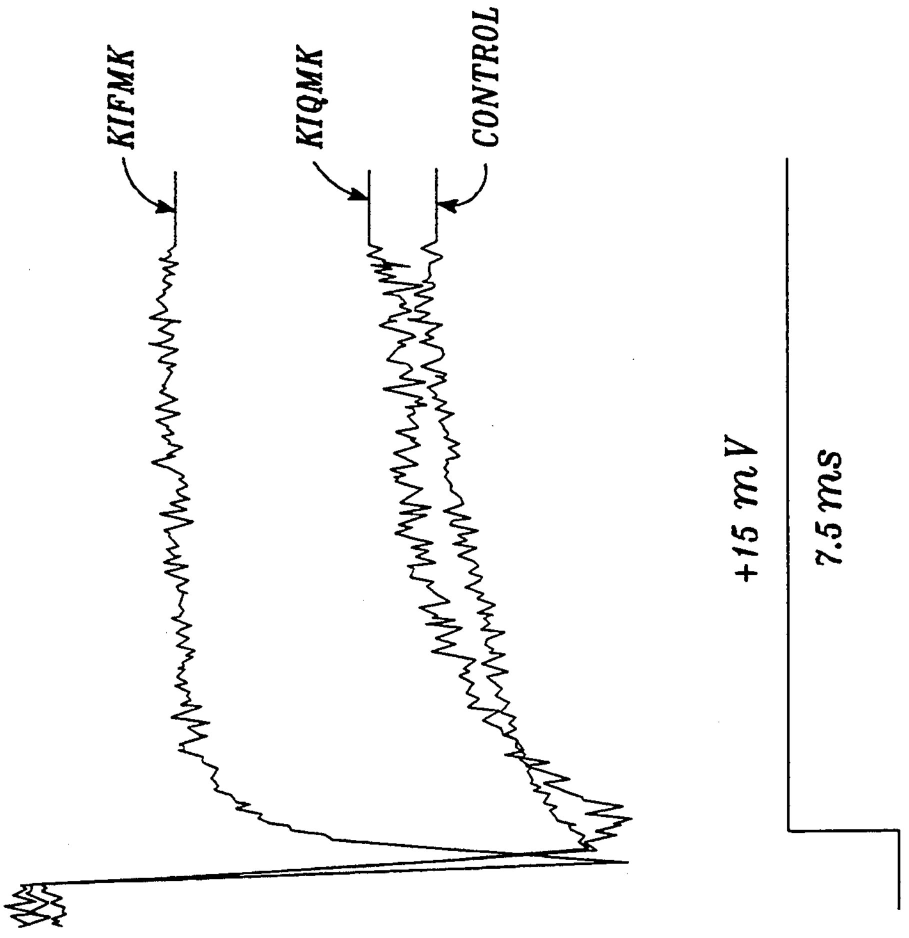
FIG. 4 shows the results of experiments (described in Example 2) in which the inactivation gate peptide KIFMK (KIFMK) was shown to restore inactivation to a mutant sodium channel by partially replacing the function of the inactivation gate. Control mutant KIQMK (KIQMK) or irrelevant peptides were without effect.

It was reasoned that if the peptide KIFMK blocks sodium channels by mimicking the sodium channel inactivation gate, it might partially restore inactivation capacity to mutant F1489Q sodium channels. Mutant F1489Q sodium channels were transiently expressed in TSQ-201 cells (24). The mutant channels in the cells activated normally but inactivated very slowly. The depolarization voltage was adjusted in a stepwise manner and test potentials from −40 to +125 mV elicited sodium currents in the mutant channels that rose rapidly but did not appreciably inactivate over 8 ms (FIG. 4). The time course of inactivation for the mutant channels was dramatically slowed over the entire voltage range. Having established the properties of the test cells and mutant channels, the peptides KIFMK and KIQMK were next tested. KIFMK or KIQMK were perfused (at a concentration of 1 mM) into the TSQ-201 cells expressing the mutant (F1489Q) sodium channels. KIFMK successfully inactivated the mutant sodium channels, while KIQMK did not (FIG. 4). Inactivation induced by 1 mM KIFMK was rapid but incomplete (i.e., not equivalent to wild-type channel function); however, a steady-state level of inhibition was reached in less than 2 ms. These results demonstrate structurally specific partial restoration of inactivation gate activity in mutant channels with the KIFMK peptide.

The combined results are highly informative because they indicate, first, that a pentapeptide can successfully enter the inactivation gate receptor of a sodium channel (i.e., access is not size or charge restricted); second, that the inactivation gate of a rapidly cycling channel is still accessible to a pentapeptide; and, third, that the KIFMK inactivation gate peptide interacts with a previously unknown inactivation gate receptor within the intracellular mouth of the transmembrane pore of the sodium channel.

EXAMPLE 3

Inactivation gate peptides compete with the normal inactivation process.

Considering binding of KIFMK inactivation gate peptide to putative inactivation gate receptor site(s) in the intracellular mouth of the sodium channel, peptide binding might prevent channel closure by the natural inactivation gate due to steric hindrance. In this model, closure of the inactivation gate would be prevented by the drug and after depolarization-induced opening, repolarization should cause the peptide to dissociate from the channel, leaving the channel open for a "brief period" of time before closure and inactivation can block the channel. The existence of the "brief period" of channel opening was captured and recorded as a rising component of tail current in the following experiments.

Figures 5A, 5B, 5C, 5D:
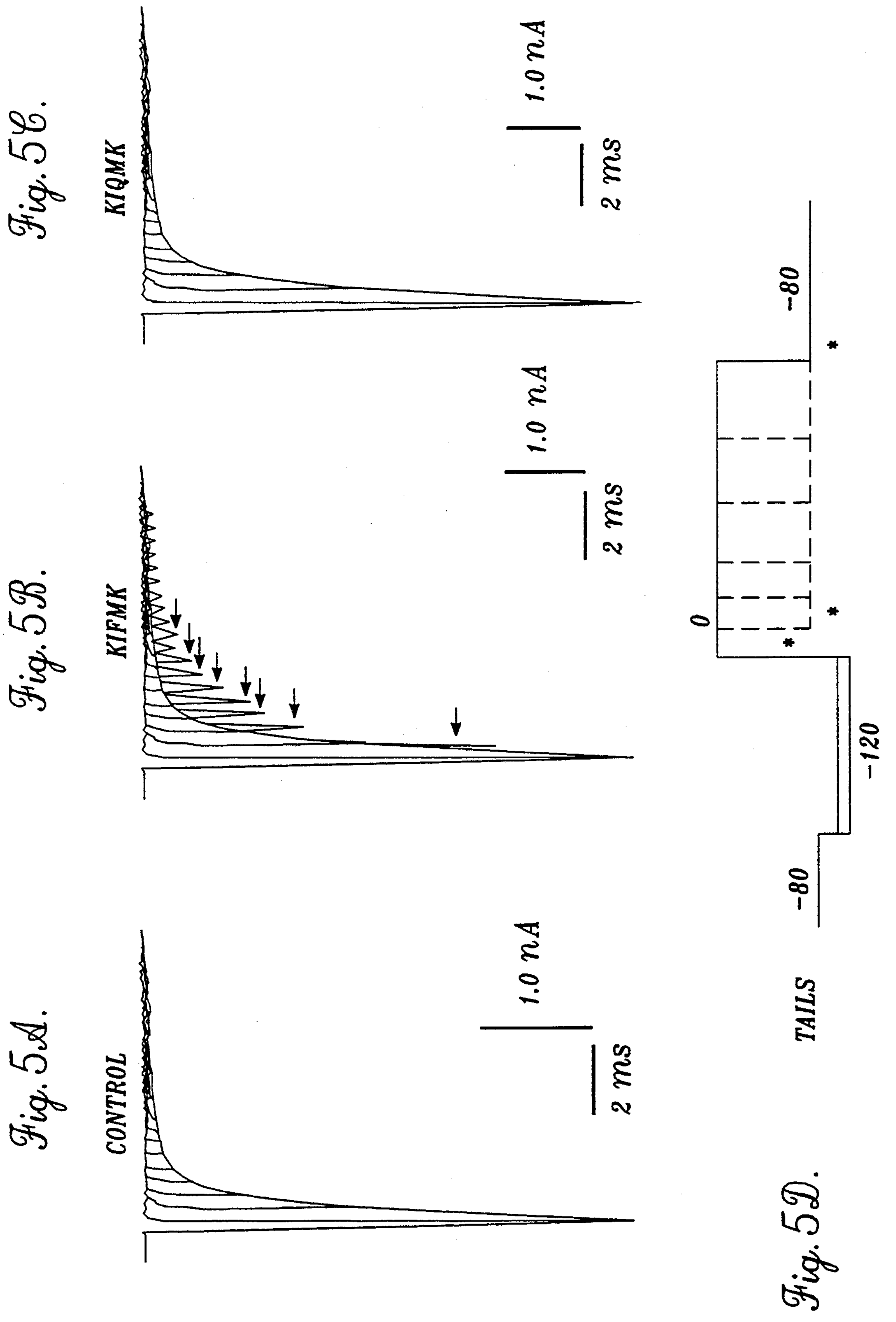
FIGS. 5A–5D show the results of experiments (described in Example 3) in which binding and then release of KIFMK inactivation gate peptide was demonstrated by measuring tail currents in patch clamped cells.

Wild-type IIA sodium channels were recorded using a whole-cell voltage clamp method. Under the recording conditions used, the sodium channels have tail currents upon rapid repolarization that declined exponentially without a rising phase because the channel rapidly closes upon repolarization (FIG. 5A). The magnitude of the tail currents decreases as the duration of the test pulse is increased. Repetitive pulsing created a family of tail current recordings that decreased exponentially (from a starting level near that of the sodium current), without any rising component in the recorded curves (FIG. 5A). In contrast, when a cell was perfused with KIFMK, a alepolarizing test pulse to 0 mV elicited a sodium current that rose rapidly to a peak and decayed with a time course faster than that of controls. Also, the tail currents elicited by a repolarization pulse (i.e., from 0 to −80 mV) rose to a peak and then decayed much more slowly than in controls (FIG. 5B). The amplitude of the rising component of the latter tail currents decreased with increasing pulse duration as the macroscopic sodium current decreased. As a control, the mutant peptide KIQMK was perfused into a test cell in an analogous fashion (i.e., by diffusion into the cytoplasm through the electrode tip), but no significant effect was observed of the mutant peptide on either macroscopic sodium currents or tail currents at any time during the period of observation (FIG. 5C).

These combined results indicate that the KIFMK peptide competes with the native inactivation gate and prevents channel closure when it is bound. Upon repolarization, KIFMK dissociates, leaving the channel briefly in an open conformation before closure and then inactivation. These results indicate that the peptide KIFMK, but not its mutant counterpart KIQMK, can compete with the normal inactivation gate for binding to a common inactivation gate receptor site within the channel, consistent with the hypothesis that the effect of the KIFMK peptide on wild-type sodium channels is by virtue of its action as an inactivation gate.

EXAMPLE 4

Inactivation gate peptides accelerate inactivation in scorpion-toxin modified wild-type sodium channels.

Figure 6:
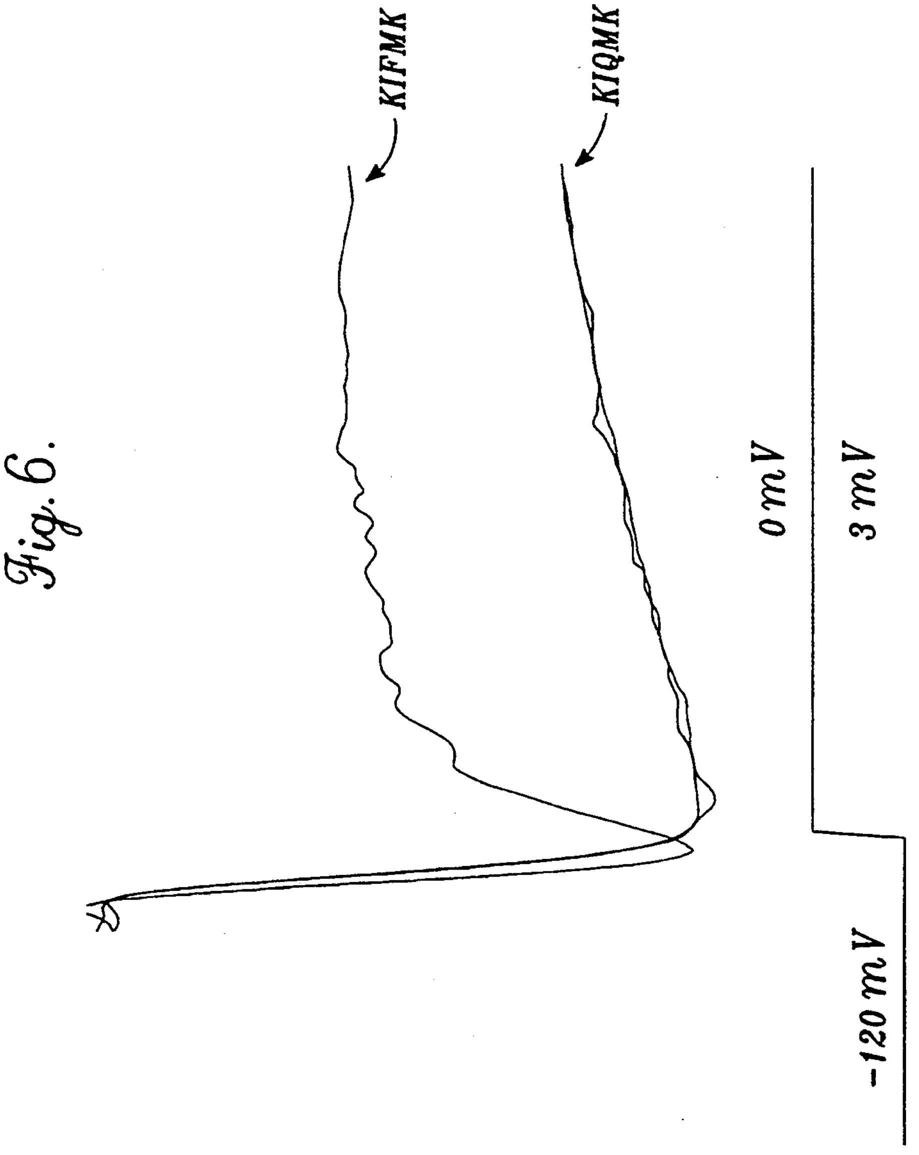
FIG. 6 shows the results of experiments (described in Example 4) in which α-scorpion toxin was used to slow the rate of sodium channel inactivation in CNaIIa cells. Addition of KIFMK was shown to cure the defect created by the scorpion toxin and partially restore inactivation activity to the channel.

Externally applied alpha-scorpion toxins slow sodium channel inactivation without affecting activation (reviewed in 26). Sodium currents in stably transfected CNaIIA-1 cells respond to a depolarizing test voltage to 0 mV with rapid activation and inactivation of the sodium channel. When 100 nM *Leiurus quinquestriatus* toxin (LqTx) was added to the bath solution in which the cells were tested, inactivation of the sodium channel was progressively impaired, resulting in a slowly inactivating sodium current (FIG. 6, control). When KIFMK was added along with α-scorpion toxin, the inactivation gate peptide overcame the effects of th toxin and the initial rate of sodium channel inactivation was significantly accelerated. KIQMK, on the other hand, had no effect (FIG. 6).

EXAMPLE 5

Structural specificity.

The effects of several inactivation gate peptides of different size and net charge have been tested for their ability to block sodium channels and to restore fast sodium channel inactivation using methods similar to those described above in Examples 1–4. The results of these experiments are summarized qualitatively below.

| PEPTIDE | M.W. | Inhibition of Na+ channels |
|---|---|---|
| acetyl-KKKFGGQDIFMTEEQKKYYNAMKK-amide (SEQ. ID. NO. 4) | 2083.6 | – |
| acetyl-QDIFMTEEQ-amide (SEQ. ID. NO. 5) | 1181 | – |
| acetyl-KDIFMTK-amide (SEQ. ID. NO. 6) | 923.2 | – |
| acetyl-KIFMK-amide | 707 | + |
| acetyl-KIQMK-amide | 687.9 | – |
| acetyl-DIFMT-amide (SEQ. ID. NO. 7) | 666.8 | – |
| IFM-amide | 408.6 | + |

None of the peptides longer than five amino acids had any effect, regardless of their net charge. From the combined results of these studies, it is concluded that peptides with a molecular mass greater than approximately 900 daltons cannot reach the inactivation gate receptor site in the wild-type sodium channel or in the F1489Q mutant. Furthermore, the peptide DIFMT, a pentamer with the wild-type sequence throughout, was ineffective. In comparison with KIFMK, this peptide has similar size, contains the critical residues IFM, but has a net negative charge. Thus, negative charge appears to inhibit entry of the inactivation gate peptide into the inactivation gate of a rapidly cycling sodium channel.

EXAMPLE 6

Structure of the inactivation gate peptide.

Figure 7:
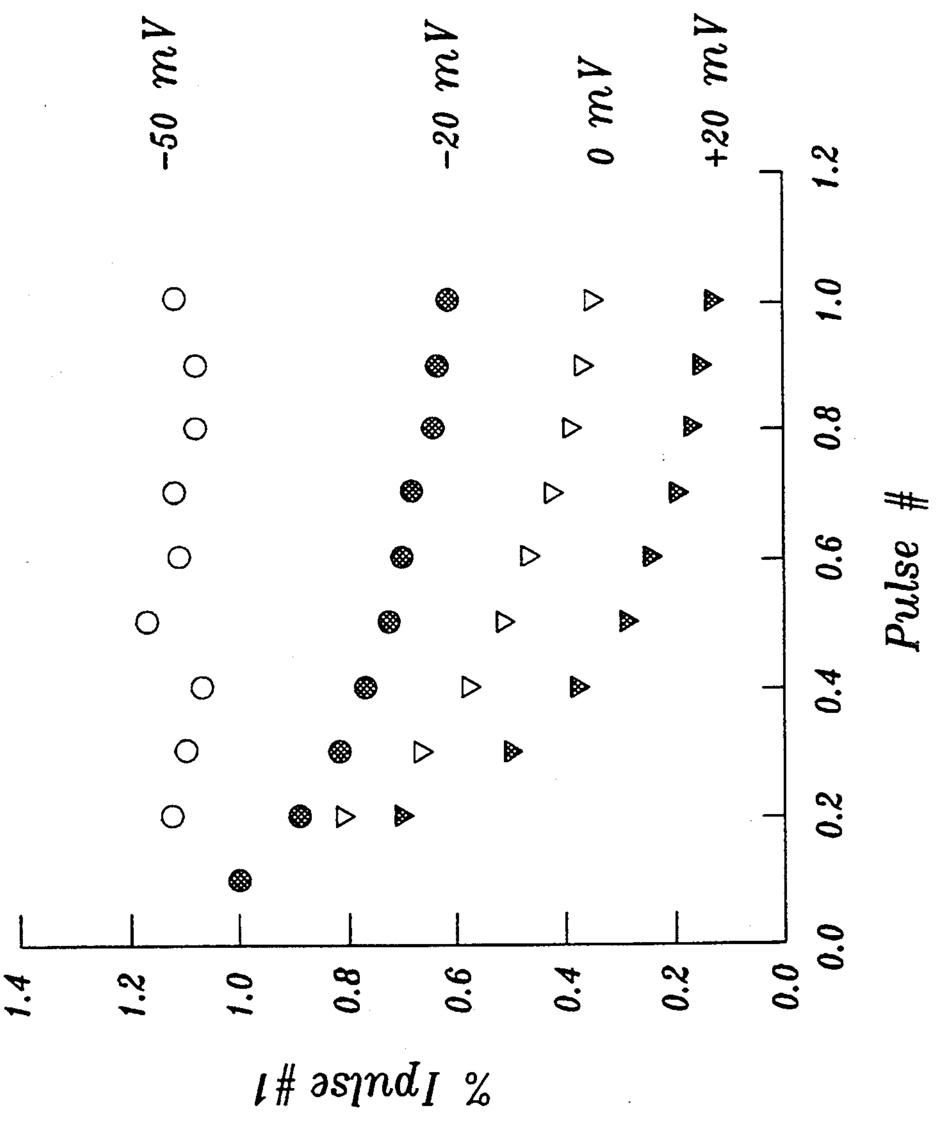
FIG. 7 shows blocking of the sodium channel in CNaIIA cells by IFM-amide (triangles) at two different applied voltage potentials, i.e., 0 mV or +20 mV, as compared with untreated controls (circles), i.e., at −50 mV or −20 mV, as described in Example 6.
Figure 8:
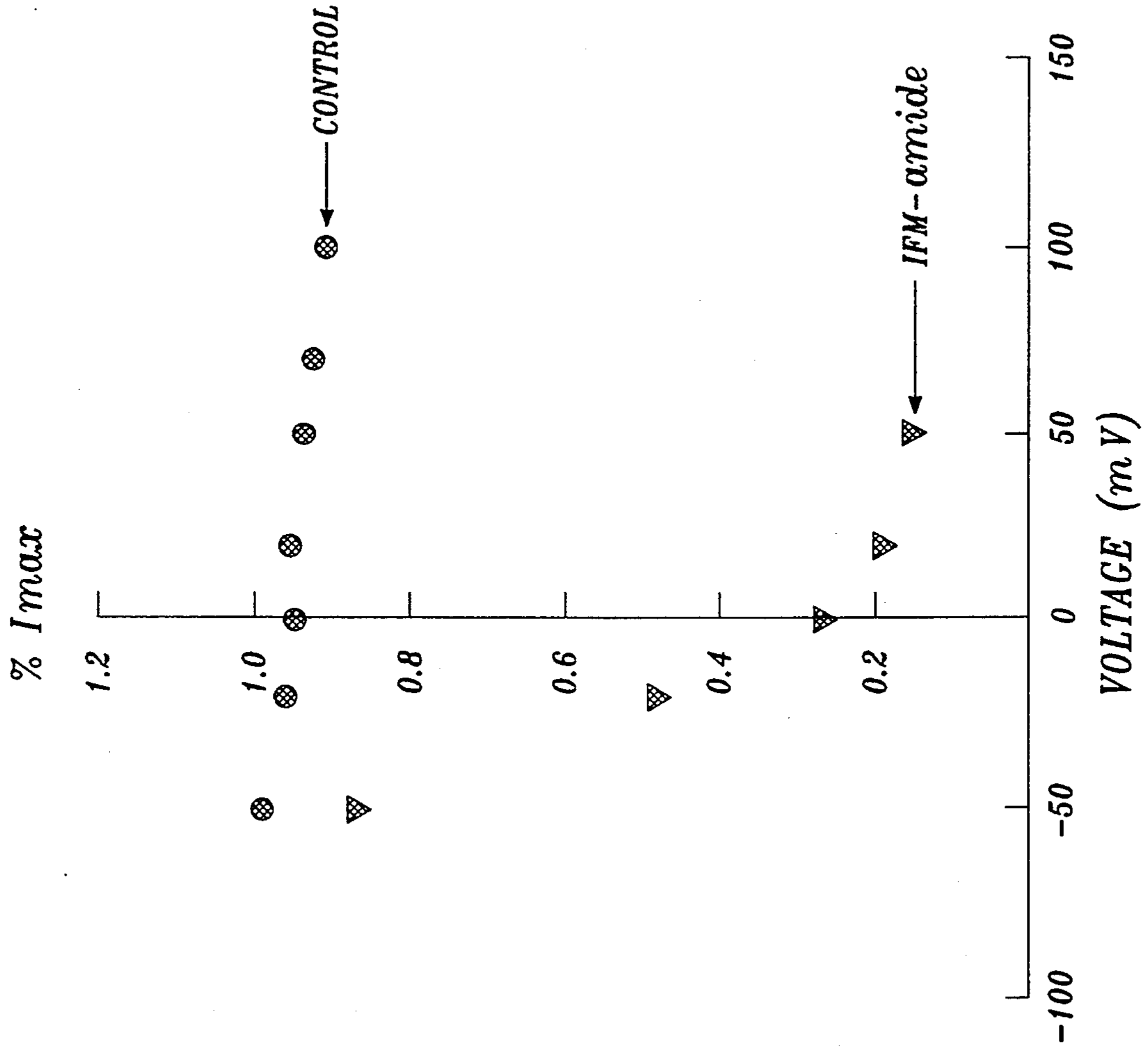
FIG. 8 shows voltage-sensitive blocking of the sodium channel by IFM-amide (triangles), compared with untreated controls (circles), as described in Example 6.

The results indicate that the IFM motif must be combined with a positive charge in order to act as an effective sodium channel blocker. It was reasoned that a tripeptide IFM-amide could be an effective inactivation gate peptide since it contains both the critical IFM residues and the charge of the unblocked α-amino group in the isoleucine residue. The IFM amide was synthesized and it was found to be a very effective sodium channel blocker (FIGS. 7 and 8). Like KIFMK, inhibition of sodium channels by IFM amide is voltage- and frequency-dependent. During repetitive stimulation, increased inhibition is observed with each succeeding pulse (pulse #) until a steady state is reached (FIG. 7). The degree of inhibition at steady state is dependent on the frequency of the stimulation pulses (% Ipulse #1; FIG. 7) and on the voltage of the stimulating pulses (FIG. 8). Surprisingly, IFM amide is an effective sodium channel blocker at much more negative membrane potentials than KIFMK despite its smaller charge (compare FIGS. 3 and 8). This implies that IFM amide has greater intrinsic affinity for the receptor site that blocks the sodium channel.

The results provide a molecular template for design of a new generation of sodium channel blockers based on the structure of the inactivation gate, an integral structural element of the sodium channel. Because the inactivation gate closes only when the sodium channel is open, these compounds will be strictly open channel blockers as demonstrated here for K1FMK and IFM-amide. The successful prediction of the structure of the new sodium channel blocker IFM amide provides proof of the concept that sodium channel blockers can be designed based on the structure of the inactivation gate. A family of sodium channel blockers based on this design principle will be valuable as antiarrhythmic, anticonvulsant, local anesthetic, analgesic, and neuroprotective drugs.

In considering the chemistry of the IFM peptide and the structure for opening and closing the inactivation gate the following considerations are useful in building a model of IFM. First, the sodium channel that is blocked by IFM has been the subject of models based on electrochemical measurements. A model for the sodium channel was constructed based on selectivity of the pore for organic cations. A hypothetical 3.1×5.1 Å rectangular channel orifice was proposed (27) lined by oxygen atoms acting as hydrogen bond acceptors during transport of organic cations and hydrated metal cations but excluding ions having nonhydrogen-bonding substituents like methyl groups. Molecular dimensions of this size approach the size of a benzene ring at about 3.2Å×3.5 Å. The transport of ions through the activated sodium channel is blocked by protonation of one or more acid groups available on the extracellular side of the channel with an acidic dissociation constant ($pK_a$) of ~5.2 (28), and it has been suggested previously that selectivity of cation transport may parallel binding of ions at a "high field strength ion-exchange site" (27) acting as a selectivity filter for the channel. This is the sodium channel that is blocked by IFM from the intracellular side. Second, the results presented above indicate that replacing phenylalanine with glutamine in IFM abolishes blocking activity (Example 1; mutant F1489Q; KIQMK) and that surrounding IFM with negative charge also results in decreased blocking activity (Example 5). The glutamine and negatively charged groups may be repelled by negative charges at the selectivity filter. The phenylalanine residue likely binds through hydrophobic interactions. Changes in the size and shape of the hydrophobic surface of this group ($R_2$) may alter the affinity or functional properties of the inactivation gate peptides. Third, a model of the inactivation gate must consider that changes in cell membrane electrical potential can rapidly and reversibly cause conformational changes in the channel protein that are transmitted down the peptide backbone to bring the inactivation gate region of the channel into contact with the inactivation gate receptor. The structural model built for the IFM inactivation gate peptides can flex from a spherical profile to a more linear molecular in response to torsional forces applied at the N- and C-terminus, and relatively small changes in the peptide bonds at Ile:Phe and Phe:Met change the planar orientation of the phenylalanine benzyl ring. Fourth, isoleucine in IFM most likely participates in hydrophobic interactions, e.g., with a methyl group in the gate receptor. Comparisons of VFM (SEQ. ID. No. 8) and GFM (SEQ. ID. No. 9) should be informative of the role of the isoleucine group in gate:receptor interactions. The structural model of IFM also shows only five potentially chemically reactive sites for derivatization and modification, namely, the ileu and phecarbonyl groups, the met carboxylic acid and the thioether, and the ileu amino group. Results from experiments like those in Example 6, above, show increased blocking activity of IFM amide compared with IFM free acid or acetyl IFM free acid. Conversion of the amine to the amide neutralizes its positive charge and reduces binding; conversion of the free acid to amide neutralizes a negative charge and adds hydrogen bonding capacity. Sixth, the results presented in Examples 1 and 2 indicate that free KIFMK peptides can block a cycling $Na^+$ channel, suggesting that the gate opens sufficiently wide to permit entry of the 14Å×24 Å IFM peptide between the receptor site, the intracellular mouth of the channel, and the gate region of the channel protein. Thus, rather surprisingly, molecular access to the gate receptor site does not appear restricted from the intracellular side. This portends well for the development of a range of derivatives with differences in blocking activity.

While the preferred embodiment of the invention has been illustrated and described, it will be appreciated that various changes can be made therein without departing from the spirit and scope of the invention.

Citations

1. Chandler, E. K., and H. Meves. Voltage clamp experiments on internally perfused giant axons. J. Physiol. Lond. 180: 788–820, 1965.

2. Armstrong, C. M. Sodium channels and gating currents. Physiol. Rev. 61:644–682, 1981.

3. Armstrong, C. M. Voltage-dependent ion channels and their gating. Physiol. Rev. 72, Suppl: 5–13, 1992.

4. Beneski, D., and W. A. Catterall. Covalent labelling of protein components of the sodium channel with a photoactivable derivative of scorpion toxin. Proc. Natl. Acad. Sci. USA 77:639–642, 1980.

5. Hartshorne, R. P., P. J. Coppersmith, and W. A. Catterall. Size characteristics of the solubilized saxitoxin receptor of the voltage-sensitive sodium channel from rat brain. J. Biol. Chem. 255:10572–10575, 1980.

6. Hartshorne, R. P., and W. A. Catterall. Purification of the saxitoxin receptor of the sodium channel from rat brain. Proc. Natl. Acad. Sci. USA 78:4620–4624, 1981.

7. Hartshorne, R. P., and W. A. Catterall. The sodium channel from rat brain. Purification and subunit composition. J. BioL Chem. 259: 1667–1675, 1984.

8. Hartshorne, R. P., D. J. Messner, J. C. Coppersmith, and W. A. Catterall. The saxitoxin receptor of the sodium channel from rat brain. Evidence for two nonidentical beta subunits. J. Biol. Chem. 257: 13888–13891, 1982.

9. Messner, D. J., and W. A. Catterall. The sodium channel from rat brain. Separation and characterization of subunits. J. Biol. Chem. 260:1597–10604, 1985.

10. Nodsa, M., S. Shimizu, T. Tanabe, T. Takai, T. Kayano, T. Ikeda, H. Takahashi, H. Nakayama, Y. Kanaoka, N. Minamino, K. Kangawa, H. Matsuo, M. Raffery, T. Hirose, S. Inayama, H. Hayashida, T. Miyata, and S. Numa. Primary structure of Electrophorus electricus sodium channel deduced from cDNA sequence. Nature Lond 312:121–127, 1984.

11. Kayano, T., M. Noda, V. Flockerzi, H. Takahashi, and S. Numa. Primary structure of rat brain sodium channel III deduced from the cDNA sequence. FEBS Lett. 228:187–194, 1988.

12. Noda, M., T. Ikeda, T. Kayano, H. Suzuki, H. Takeshima, M. Kurasaki, H. Takahashi, and S. Numa. Existence of distinct sodium channel messenger RNAs in rat brain. Nature Lond. 320: 188–192, 1986.

13. Sarao, R., S. K. Gupta, V. J. Auld, and R. J. Dunn. Developmentally regulated alternative RNA splicing of rat brain sodium channel mRNAs. Nucleic Acids Res. 19:5673–5679, 1991.

14. Yrowsky, P. J., B. K. Krueger, C. E. Olson, E. C. Clevinger, and R. D. Koos. Brain and heart sodium channel subtype mRNA expression in rat cerebral cortex. Proc. Natl. Acad. Sci. USA 88:9453–9457, 1991.

15. Auld, V. J., A. L. Goldin, D. S. Krafte, J. Marshall, J. M. Dunn, W. A. Catterall, H. A. Lester, N. Davidson, and R. J. Dunn. A rat brain $Na^+$ channel alpha subunit with novel gating properties. Neuron 1:449–461, 1988.

16. Goldin, A. L., T. Snutch, H. Lubbert, A. Dowsett, J. Marshall, V. Auld, W. Downey, L. C. Fritz, H. A. Lester, R. Dunn, W. A. Catterall, and N. Davidson. Messenger RNA coding for only the α subunit of the rat brain NA channel is sufficient for expression of functional channels in Xenopus oocytes. Proc. Natl. Acad. Sci USA 83:7503-7507, 1986.

17. Kallen, R. G., Z. H. Sheng, J. Yang, L. Q. Chen, R. B. Rogart, and R. L. Barchi. Primary structure and expression of a sodium channel characteristic of deenervated and immature rat skeletal muscle. Neuron 4:233-242, 1990.

18. Rogart, R. B., L. L. Cribbs, L. K. Muglia, D. D. Kephart, and M. W. Kaiser. Molecular cloning of a putative tetrodotoxin-resistant rat heart sodium channel isoform. Proc. Natl. Acad. Sci. USA 86:8170-8174, 1989.

19. Trimmer, J. S., S. S. Cooperman, S. A. Tomiko, J. Y. Zhou, S. M. Crean, M. B. Boyle, R. G. Kallen, Z. H. Sheng, R. L. Barchi, F. J. Sigworth, R. H. Goodman, W. S. Agnew, and G. Mandel. Primary structure and functional expression of a mammalian skeletal muscle sodium channel. Neuron 3:33-49, 1989.

20. Vassilev, P. M., T. Scheuer, and W. A. Catterall. Identification of an intracellular peptide segment involved in sodium channel inactivation. Science Wash. DC 241: 1658-1661, 1988.

21. Vassilev, P. M., T. Scheuer, and W. A. Catterall. Inhibition of inactivation of single sodium channels by a site-directed antibody. Proc. Natl. Acad. Sci. USA 86: 8147-8151, 1989.

22. Stühmer, W. F. Conti, H. Suzuki, X. Wang, M. Noda, N. Yahadi, H. Kubo, and S. Numa. Structural parts involved in activation and inactivation of the sodium channel. Nature Lond. 339: 597-603, 1989

23. West, J. W., T. Scheuer, L. Maechler, and W. A. Catterall. Neuron 8:59-70, 1988.

24. Margolskee, R. F., B. McHendry-Rinde, and R. Horn. Soc. for Neurosci. Abst. 18:644, 1992.

25. Ukomadu, C., J. Zhou, F. J. Sigworth and W. S. Agnew. Neuron 8:663-676, 1992.

26. Catterall, W. A. Ann. Rev. Pharmacol. Toxicol. 20:15-43, 1980.

27. Hille, B. The permeability of the sodium channel to metal cations in myelinated nerve. J. Gen. Physiol. 59:637-658, 1972.

28. Hille, B. Pharmacological modifications of the sodium channels of frog nerve. J. Gen. Physiol. 51:199-219, 1968.

SEQUENCE LISTING ( 1 ) GENERAL INFORMATION:

( i i i ) NUMBER OF SEQUENCES:9

( 2 ) INFORMATION FOR SEQ ID NO:1:

( i ) SEQUENCE CHARACTERISTICS:
( A ) LENGTH:3 amino acids
( B ) TYPE:amino acid
( D ) TOPOLOGY:linear ( i i ) MOLECULE TYPE:peptide
( A ) DESCRIPTION:page 3, lines 29-30; IFM ( i x ) SEQUENCE DESCRIPTION: SEQ ID NO:1:

Ile Phe Met ( 2 ) INFORMATION FOR SEQ ID NO:2:

( i ) SEQUENCE CHARACTERISTICS:
( A ) LENGTH:5 amino acids
( B ) TYPE:amino acid
( D ) TOPOLOGY:linear ( i i ) MOLECULE TYPE:peptide
( A ) DESCRIPTION:page 4, line 13; KIQMK ( i x ) SEQUENCE DESCRIPTION: SEQ ID NO:2:

Lys Ile Gln Met Lys
5

( 2 ) INFORMATION FOR SEQ ID NO:3:

( i ) SEQUENCE CHARACTERISTICS:
( A ) LENGTH:5 amino acids
( B ) TYPE:amino acid
( D ) TOPOLOGY:linear ( i i ) MOLECULE TYPE:peptide
( A ) DESCRIPTION:page 5, line 4; KIFMK ( i x ) SEQUENCE DESCRIPTION: SEQ ID NO:3:

Lys Ile Phe Met Lys
5

-continued ( 2 ) INFORMATION FOR SEQ ID NO:4:

( i ) SEQUENCE CHARACTERISTICS:
( A ) LENGTH:24 amino acids
( B ) TYPE:amino acid
( D ) TOPOLOGY:linear ( i i ) MOLECULE TYPE:polypeptide
( A ) DESCRIPTION:page 20, line 7; KKKFGGQDIFMTEEQKKYYNAMKK ( i x ) SEQUENCE DESCRIPTION: SEQ ID NO:4:

```
Lys Lys Lys Phe Gly Gly Gln Asp Ile Phe Met Thr Glu Glu Gln
                5                   10                  15

Lys Lys Tyr Tyr Asn Ala Met Lys Lys
                20
```

( 2 ) INFORMATION FOR SEQ ID NO:5:

( i ) SEQUENCE CHARACTERISTICS:
( A ) LENGTH:9 amino acids
( B ) TYPE:amino acid
( D ) TOPOLOGY:linear ( i i ) MOLECULE TYPE:peptide
( A ) DESCRIPTION:page 20, line 7; QDIFMTEEQ ( i x ) SEQUENCE DESCRIPTION: SEQ ID NO:5:

```
Gln Asp Ile Phe Met Thr Glu Glu Gln
                5
```

( 2 ) INFORMATION FOR SEQ ID NO:6:

( i ) SEQUENCE CHARACTERISTICS:
( A ) LENGTH:7 amino acids
( B ) TYPE:amino acid
( D ) TOPOLOGY:linear ( i i ) MOLECULE TYPE:peptide
( A ) DESCRIPTION:page 20, line 7; KDIFMTK ( i x ) SEQUENCE DESCRIPTION: SEQ ID NO:6:

```
Lys Asp Ile Phe Met Thr Lys
                5
```

( 2 ) INFORMATION FOR SEQ ID NO:7:

( i ) SEQUENCE CHARACTERISTICS:
( A ) LENGTH:5 amino acids
( B ) TYPE:amino acid
( D ) TOPOLOGY:linear ( i i ) MOLECULE TYPE:peptide DIFMT
( A ) DESCRIPTION:page 20, line 7; DIFMT ( i x ) SEQUENCE DESCRIPTION: SEQ ID NO:7:

```
Asp Ile Phe Met Thr
                5
```

( 2 ) INFORMATION FOR SEQ ID NO:8:

( i ) SEQUENCE CHARACTERISTICS:
( A ) LENGTH:3 amino acids
( B ) TYPE:amino acid
( D ) TOPOLOGY:linear ( i i ) MOLECULE TYPE:peptide
( A ) DESCRIPTION:page 22, line 17; VFM ( i x ) SEQUENCE DESCRIPTION: SEQ ID NO:8:

```
Val Phe Met
```

-continued ( 2 ) INFORMATION FOR SEQ ID NO:9:

( i ) SEQUENCE CHARACTERISTICS:
( A ) LENGTH:3 amino acids
( B ) TYPE:amino acid
( D ) TOPOLOGY:linear ( i i ) MOLECULE TYPE:peptide
( A ) DESCRIPTION:page 22, line 17; GFM ( i x ) SEQUENCE DESCRIPTION: SEQ ID NO:9:

G l y · P h e M e t

The embodiments of the invention in which an exclusive property or privilege is claimed are defined as follows:

1. An assay for identifying a compound which inactivates a sodium channel by binding to the inactivation gate receptor of said channel, thereby preventing the activation gate of said channel from binding to said receptor, comprising the steps of:

establishing first and a second cultures of cells having a wild-type sodium channel and third and a fourth cultures of cells having a noninactivating mutant sodium channel, measuring a baseline sodium current for one or more cells in the first and the second cultures, and a baseline inactivation rate for one or more cells in the third and the fourth cultures, treating the cells in the first and the third cultures with a candidate inhibitor, and the cells in the second and the fourth cultures, with an inactive control peptide, measuring a test sodium current in one or more cells in the first and the second cultures, and a test inactivation rate in one or more cells in the third and the fourth cultures, repeating the previous four steps, except that the cells in the first and the third cultures are treated with an IFM amide control, and determining that the candidate inhibitor is an inactivation gate inhibitor of the sodium channel if the test sodium current of the cells in the first culture is lower than the baseline of the first culture, the test sodium current of the cells in the second culture is about equal to the baseline of the second culture, the test inactivation rate of the cells in the third culture is higher than the baseline of the third culture, the test inactivation rate of the cells in the fourth culture is about equal to the baseline of the fourth culture, and the candidate inhibitor restores sodium channel inactivation in cells of the third culture to an extent at least equal to the IFM amide control, wherein said candidate inhibitor comprises:

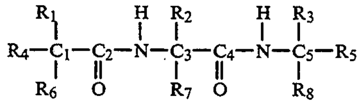

(I)

wherein $R_1$ is straight or branched chain alkyl having a neutral charge; $R_2$ comprises an aryl group; $R_3$ is a straight or branched chain thio-alkyl or alkyl chain having a neutral charge; either $R_4$ or $R_5$ or both are positively charged groups; and $R_6$, $R_7$, and $R_8$ are hydrogen atoms.

* * * * *

UNITED STATES PATENT AND TRADEMARK OFFICE

CERTIFICATE OF CORRECTION

PATENT NO. : 5,437,982

DATED : August 1, 1995

INVENTOR(S) : W.A. Catterall et al.

It is certified that error appears in the above-indentified patent and that said Letters Patent is hereby corrected as shown below:

On the title page:

| | | |
|---|---|---|
| [56] (pg. 2, col. 1) | Refs. Cited Other Pubs. Pub. No. 2 | "natl." should read --*Natl.*-- |
| [56] (pg. 2, col. 1) | Refs. Cited Other Pubs. | Insert --Ukomadu, C., J. Zhou, F.J. Sigworth and W.S. Agnew. *Neuron* 8:663-676, 1992.-- |
| [56] (pg. 2, col. 2) | Refs. Cited Other Pubs. Pub. No. 7 | "Cluster" should read --cluster-- |

| Column | Line | |
|---|---|---|
| 1 | 7 | "5-RO1NS15751" should read --5-R01NS15751-- |
| 3 | 1 | "(isoleucine- phenylalanine-methionine;" should read (isoleucine-phenylalanine-methionine;-- |
| 4 | 63 | "2)the" should read --2) the-- |
| 7 | 6 | "ting" should read --ring-- |
| 7 | 7 | "ting" should read --ring-- |
| 7 | 58 | "depolafizing" should read --depolarizing-- |

UNITED STATES PATENT AND TRADEMARK OFFICE

CERTIFICATE OF CORRECTION

PATENT NO. : 5,437,982

DATED : August 1, 1995

INVENTOR(S) : W.A. Catterall et al.

It is certified that error appears in the above-indentified patent and that said Letters Patent is hereby corrected as shown below:

| COLUMN | LINE | |
|---|---|---|
| 15 | 38 | "th" should read --the scorpion-- |
| 16 | 42 | "K1FMK" should read --KIFMK-- |
| 18 | 28 | "BioL" should read --*Biol.*-- |
| 21 | 52 | "Val Phe Met" should read --Val Phe Met 3-- |
| 23 | 10 | "Gly Phe Met" should read --Gly Phe Met 3-- |

Signed and Sealed this

Twenty-sixth Day of December, 1995

Attest:

BRUCE LEHMAN

*Attesting Officer*

*Commissioner of Patents and Trademarks*